(12) United States Patent
Wang

(10) Patent No.: US 9,833,148 B2
(45) Date of Patent: Dec. 5, 2017

(54) METHODS AND SYSTEMS FOR INTEGRATED IMAGING USING OPTICAL COHERENCE TOMOGRAPHY AND PHOTOACOUSTIC IMAGING

(75) Inventor: Ruikang K. Wang, Seattle, WA (US)

(73) Assignee: University of Washington Through its Center For Commerciallzation, Seattle, WA (US)

( * ) Notice: Subject to any disclaimer, the term of this patent is extended or adjusted under 35 U.S.C. 154(b) by 320 days.

(21) Appl. No.: 14/234,197

(22) PCT Filed: Aug. 13, 2012

(86) PCT No.: PCT/US2012/050577
§ 371 (c)(1),
(2), (4) Date: Mar. 19, 2014

(87) PCT Pub. No.: WO2013/023210
PCT Pub. Date: Feb. 14, 2013

(65) Prior Publication Data
US 2014/0185055 A1    Jul. 3, 2014

Related U.S. Application Data

(60) Provisional application No. 61/522,627, filed on Aug. 11, 2011.

(51) Int. Cl.
*G01B 9/02*      (2006.01)
*A61B 5/00*      (2006.01)
(52) U.S. Cl.
CPC .......... *A61B 5/0095* (2013.01); *A61B 5/0035* (2013.01); *A61B 5/0066* (2013.01);
(Continued)

(58) Field of Classification Search
CPC . G01B 9/02091; A61B 5/0035; A61B 5/0066; A61B 5/0073; A61B 5/0095; A61B 3/102
See application file for complete search history.

(56) References Cited

U.S. PATENT DOCUMENTS 5,479,259 A * 12/1995 Nakata .................... G01K 5/52
356/432
6,657,727 B1 * 12/2003 Izatt .................... G01N 21/4795
356/450
(Continued)

FOREIGN PATENT DOCUMENTS

WO   WO 2009055705 A2 * 4/2009 .......... A61B 5/0059
WO   2010/080991     7/2010
WO   2010/086861     8/2010

OTHER PUBLICATIONS

Edney, Paul A. et al. "Acoustic modulation and photon-phonon scattering in optical coherence tomography". Applied Optics, vol. 40, No. 34, Dec. 1, 2001, pp. 6381-6388.*
(Continued)

*Primary Examiner* — Michael A Lyons
(74) *Attorney, Agent, or Firm* — McDonnell Boehnen Hulbert & Berghoff LLP

(57) ABSTRACT

Systems and methods for photoacoustic imaging are provided. Photoacoustic signals are excited from a body and the excited photoacoustic signals are detected with a low coherence interferometer system serving as a photoacoustic detector. Cross-sectional images of the body are then reconstructed by the system from the detected photoacoustic signals.

20 Claims, 6 Drawing Sheets

(52) U.S. Cl.
CPC .......... *A61B 5/0084* (2013.01); *A61B 5/7203* (2013.01); *A61B 5/725* (2013.01); *G01B 9/02091* (2013.01)

(56) References Cited

U.S. PATENT DOCUMENTS

| | | | | |
|---|---|---|---|---|
| 2003/0020922 | A1* | 1/2003 | Crowley | A61B 5/0066 356/502 |
| 2006/0061769 | A1* | 3/2006 | Yang | G02B 21/0056 356/479 |
| 2008/0108867 | A1 | 5/2008 | Zhou et al. | |
| 2010/0094134 | A1 | 4/2010 | Zhu et al. | |
| 2010/0245770 | A1 | 9/2010 | Zhang et al. | |
| 2010/0268042 | A1* | 10/2010 | Wang | A61B 5/0059 600/322 |
| 2011/0096294 | A1 | 4/2011 | Peyman | |
| 2011/0098572 | A1 | 4/2011 | Chen et al. | |
| 2011/0282192 | A1 | 11/2011 | Axelrod et al. | |
| 2012/0092616 | A1 | 4/2012 | Peyman | |
| 2012/0271204 | A1* | 10/2012 | Peyman | A61B 5/0095 601/2 |

OTHER PUBLICATIONS

Huang, Chuanyong et al. "Ultrasound-enhanced optical coherence tomography: improved penetration and resolution". Journal of the Optical Society of America A, vol. 25, Issue 4, 2008, pp. 938-946.*
International Search Report PCT/US2012/050577, dated Dec. 3, 2012.
Li et al., Three-dimensional combined photoacoustic and optical coherence microscopy for in vivo microcirculation studies, 17 Optics Express, 16450 (2009).
Jiao et al., Simultaneous multimodal imaging with integrated photoacoustic microscopy and optical coherence tomography, 34 Optics Letters, 2961 (2009).
L. V. Wang, Multiscale photoacoustic microscopy and computed tomography, Nature Photonics, 3:503-509 (2009).
L. V. Wang, Prospects of photoacoustic tomography, Medical physics, 35(12):5758-5767 (2008).
H. F. Zhang, K. Maslov, G. Stoica, and L. V. Wang, Functional photoacoustic microscopy for high-resolution and noninvasive in vivo imaging, Nature Biotechnology 24,848-851 (Jul. 2006).
S. S. Oladipupo, S. Hu, A. C. Santeford, J. Yao, J. Kovalski, R.V. Shohet, K. Maslov, L. V. Wang, and J. M. Arbeit, Conditional HIF-1 induction produces multistage neovascularization with stage-specific sensitivity to VEGFR inhibitors and myeloid cell independence, Blood, 117(15), 4142-4153 (2011).
R. O. Esenaliev, A. A. Karabutov, and A. A. Oraevsky, Sensitivity of laser opto-acoustic imaging in detection of small deeply embedded tumors, IEEE Journal of Selected Topics in Quantum Electronics, 5(4):981-988 (1999).
C. Kim, T. N. Erpelding, L. Jankovic, M. D. Pashley, and L. V. Wang, Deeply penetrating in vivo photoacoustic imaging using a clinical ultrasound array system, Biomedical Optics Express, 1(1): 278-284 (2010).
R. A. Kruger, D. R. Reinecke, and G. A. Kruger, Thermoacoustic computed tomography—technical considerations, Medical physics, 26(9):1832-1837 (1999).
K. Maslov, H. F. Zhang,S. Hu, and L. V. Wang, Opticalresolution photoacoustic microscopy for in vivo imaging of single capillaries, Optics Letters, 33(9):929-931 (2008).
S. Hu, K. Maslov, and L. V. Wang, Second-generation optical resolution photoacoustic microscopy with improved sensitivity and speed, Optics Letters, 36(7):1134-1136 (2011).
T. Berer, A. Hochreiner, S. Zamiri, and P. Burgholzer, Remote photoacoustic imaging on solid material using a two wave mixing interferometer, Optics Letters, 35(24):4151-4153 (2010).
B. F. Pouet, R. K. Ing, S. Krishnaswamy, and D. Royer, Heterodyne interferometer with two-wave mixing in photorefractive crystals for ultrasound detection on rough surfaces, Applied Physics Letters, 69(26):3782-3784 (1996).
M. Paul, B. Betz, and W. Arnold, Interferometric detection of ultrasound at rough surfaces using optica phase conjugation, Applied Physics Letters, 50(22):1569-1571 (1987).
S. A. Carp, A. Guerra, S. Q. Duque, and V. Venugopalan, Optoacoustic imaging using interferometric measurement of surface displacement, Applied Physics Letters, 85(23):5772- 5774 (2004).
E. Zhang, J. Laufer, and P. Beard, Backward-mode multiwavelength photoacoustic scanner using a planar Fabry-Perot polymer film ultrasound sensor for high resolution three-dimensional imaging of biological tissues, Applied Optics, 47(4):561-577 (2008).
G. Paltauf, R. Nuster, M. Haltmeier, and P. Burgholzer, Photoacoustic tomography using a Mach-Zehnder interferometer as an acoustic line detector, Applied Optics, 46(16):3352-3358 (2007).
L. Li, K. Maslov, G. Ku, and L. V. Wang, Three-dimensional combined photoacoustic and optical coherence microscopy for in vivo microcirculation studies, Optics Express, 17(19):16450-16455 (2009).
S. Jiao, Z. Xie, H. F. Zhang, and C. A. Puliafito, Simultaneous multimodal imaging with integrated photoacoustic microscopy and optical coherence tomography, Optics Letters, 34(19):2961-2963 (2009).
E. Z. Zhang, J. Laufer, B. Považay, A. Alex, B. Hofer, W. Drexler, P. Beard, Multimodal simultaneous photoacoustic tomography, optical resolution microscopy and OCT system, Proc. SPIE, 75640U-7 (2010).
T. Liu, Q. Wei, J. Wang, S. Jiao, and H. F. Zhang, Combined photoacoustic microscopy and optical coherence tomography can measure metabolic rate of oxygen, Biomedical Optics Express, 2(5):1359-1365(2011).
Y. Wang, D. Xing, Y. Zeng, and Q. Chen, Photoacoustic imaging with deconvolution algorithm, Physics in Medicine and Biology, 49:3117-3124 (2004).

* cited by examiner

METHODS AND SYSTEMS FOR INTEGRATED IMAGING USING OPTICAL COHERENCE TOMOGRAPHY AND PHOTOACOUSTIC IMAGING

CROSS-REFERENCE TO RELATED APPLICATIONS

This application claims priority to U.S. Provisional Patent Application Ser. No. 61/522,627 filed on Aug. 11, 2011, which is hereby incorporated by reference in its entirety.

BACKGROUND

Photoacoustic imaging (PAI) is used as a tool to investigate endogenous tissue components. In PAI, non-ionizing laser pulses are delivered into endogenous tissues; some of the delivered energy is absorbed and converted into heat, leading to thermoelastic expansion and consequent ultrasonic emission. The generated ultrasonic waves are then typically detected by ultrasonic transducers and are used to form images.

The absorption of the delivered energy in endogenous tissues can be due to molecules such as hemoglobin, for example. PAI thus provides a unique ability to image hemodynamics within microcirculatory tissue beds in vivo.

Current photoacoustic microscopy employs a confocal configuration to achieve imaging with optical-resolution for endogenous tissues with a maximal penetration depth of approximately 1.0 mm. Because of the strong attenuation of ultrasound waves in air, acoustic coupling (i.e., physical contact) between a sample and an acoustic transducer is typically required for ultrasound detection. This requirement can make photoacoustic imaging of biological samples difficult, limiting its practical applicability.

There is a need for a method and system for noncontact PAI that provides stable photoacoustic detection for imaging a sample.

SUMMARY

In accordance with the present invention, systems and methods are defined for photoacoustic imaging. In one embodiment, the method may comprise exciting photoacoustic signals from a body and detecting the photoacoustic signals with a low coherence interferometer system, wherein the low coherence interferometer system serves as a photoacoustic detector. The method may further comprise reconstructing cross-sectional images of the body from the detected photoacoustic signals.

In another embodiment, systems for photoacoustic imaging are provided. In one embodiment, the system comprises an optical coherence tomography probe, a laser, an optical circulator, a coupler, and a photodetector. The optical tomography probe and the laser are combined by a dichroic mirror onto a sample to excite photoacoustic signals from the sample. The excited photoacoustic signals are coupled from the coupler with an output from the optical circulator into the photodetector, and the photodetector is connected with a data acquisition unit and a computing system for image reconstruction of the sample.

In yet another embodiment, a physical computer-readable storage medium having stored thereon instructions executable by a device to cause the device to perform functions is provided. The functions include exciting photoacoustic signals from a body, detecting the photoacoustic signals with an optical coherence tomography system, wherein the optical coherence tomography system serves as a photoacoustic detector. The functions further include reconstructing cross-sectional images of the body from the detected photoacoustic signals.

The systems and methods provide noncontact photoacoustic imaging by using a low coherence interferometer as the acoustic detector. The low coherence interferometer may be an optical coherence tomography (OCT) system. The OCT system may further generate an image of a sample independent of or in addition to the method for photoacoustic imaging. The OCT system may comprise a light source, an excitation laser, a circulator, a fiber coupler, a photodetector, a high-pass filter, a data acquisition unit, and a computing system. The light source is routed through the circulator and the fiber coupler to form a probe beam, and a dichroic mirror combines and directs the probe beam and the excitation laser onto the body. The probe beam may be focused onto the surface of the body, while the excitation laser may be focused into the body so as to excite photoacoustic signals from the body. The emitted photoacoustic signals are directed through the fiber coupler and the circulator into the photodetector. The photoacoustic signals are then directed through the high-pass filter to the data acquisition unit. The data acquisition unit then sends information regarding the photoacoustic signals to the computing system for processing into images.

When a DC output signal from the photodetector crosses a threshold, a trigger signal may be sent from the computing system to the data acquisition unit to sample the photoacoustic signals, and another trigger signal may be sent from the computing system to initiate the excitation laser.

The OCT system may be a time domain system operating in a homodyne mode. The detection bandwidth for each of the photoacoustic signals may be increased by increasing the speed of the photodetector and/or decreasing the size of the probe beam of the OCT system.

These as well as other aspects and advantages will become apparent to those of ordinary skill in the art by reading the following detailed description, with reference where appropriate to the accompanying drawings.

DETAILED DESCRIPTION

In the following detailed description, reference is made to the accompanying figures, which form a part thereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Figure 1:
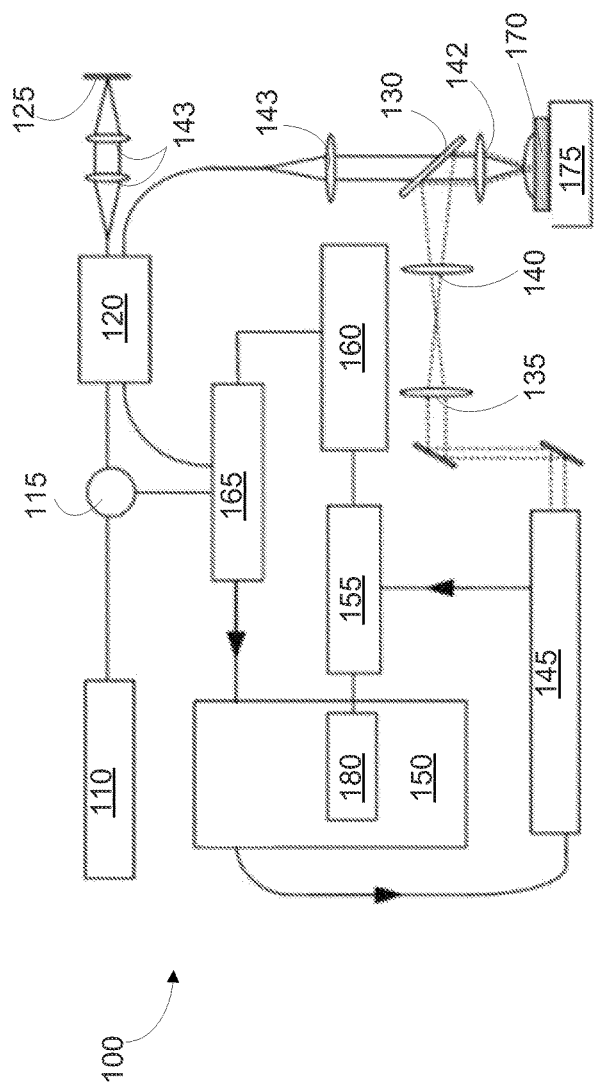
FIG. 1 depicts a schematic of an exemplary photoacoustic imaging system in accordance with at least one embodiment.

FIG. 1 depicts a schematic of an exemplary photoacoustic imaging system 100, in accordance with at least one embodiment. In the example system 100, an optical coherence tomography (OCT) system is shown. In other example embodiments, however, another type of low coherence interferometer (LCI) may be used. The system 100 may include a light source 110, a nonreciprocal optical element 115, a fiber coupler 120, a reference mirror 125, a dichroic mirror 130, a first lens 135, a second lens 140, a third lens 142, and a laser 145. A plurality of additional lenses 143 may also be present. The system 100 may further include a computing system 150, a data acquisition unit 155, a signal processing unit 160, and a photodetector 165. A sample or body 170 to be imaged rests on a platform 175.

The OCT system may be a time domain OCT system operating in homodyne mode.

In one example embodiment, the light source 110 may be a low temporally coherent light source, such as a superluminescent diode. In other example embodiments, the light source 110 may be an ultrashort pulsed laser or a supercontinuum laser. In yet another example, the light source 110 may be a wavelength-swept laser. Still other light sources may be used. In one example embodiment, the light source 110 may have a central wavelength of about 1310 nm and a spectral bandwidth of about 46 nm.

In one example embodiment, the laser 145 may be a Q-switched Nd:YAG laser, and may be directed at the sample 170 and operated at about 532 nm. The repetition rate and the pulse width of the laser 145 may be about 10 Hz and 7 ns, respectively. A beam or a plurality of beams emitted from the laser 145 may be designed to induce displacement (e.g., vibration) at the sample 170.

The first lens 135 and the second lens 140 may each comprise antireflection-coated plane convex diode laser lenses to focus the laser beams. In one example embodiment, each of the first and second lenses 135, 140 may be an objective lens with a focal length of about 50 mm.

The nonreciprocal optical element 115 may be an optical circulator, and may have a first port connected to receive light from the light source 110. The nonreciprocal optical element 115 may further include a second port that may direct light from the first port to the fiber coupler 120 and receive light back from the fiber coupler 120, and a third port for directing light received from the fiber coupler 120 to the photodetector 165.

The fiber coupler 120 serves as a beamsplitter, which transmits or splits some fraction of the power of the incident light power from the light source 110 into each of a sample arm 112 and a reference arm 114. Light returning from both the sample and the reference arms 112 and 114 may be fed to the photodetector 165 via the nonreciprocal optical element 115. In one example embodiment, the fiber coupler 120 may comprise a pair of fibers partially fused together. The fiber coupler may be a 2×2 fiber coupler.

The reference mirror 125 serves to reflect light directed from the fiber coupler 120 back to the fiber coupler 120.

The fiber coupler 120 feeds light to the dichroic mirror 130. The dichroic mirror 130 transmits the light from the light source 110, but deflects the light from the laser 145. The transmitted and deflected lights are then focused by the third lens 142 onto the sample 170.

The photodetector 165 serves to reject common-mode light intensity noise from photoacoustic signals received from the fiber coupler 120 and/or the nonreciprocal optical element 115. The photodetector 165 then feeds the photoacoustic signals to the signal processing unit 160.

The signal processing unit 160 separates the photoacoustic signals from the low frequency signals. In one example embodiment, the signal processing unit 160 may be a high-pass filter.

The data acquisition unit 155 is fed photoacoustic signals output from the photodetector 165 and/or the signal processing unit 160 and is configured to change the photoacoustic signals to digital information that the data acquisition unit 155 may then send to the computing system 150 for further processing. The digital information may be sent to the computing system 150 via a GPIB interface card 180, for example. The signals from the photodetector 165 may pass through the signal processing unit 160 before being fed to the data acquisition unit 155. In one example embodiment, the data acquisition unit 155 may be an oscilloscope, such as a digital oscilloscope. The digital oscilloscope may have a sampling frequency of 250 MHz. The laser 145 may send a trigger signal to the data acquisition unit 155 so that the data acquisition is synchronized with the laser pulse from the laser 145.

The computing system 150 may include a processor, data storage, and memory. These elements may be coupled by a system or bus or other mechanism. The processor may include one or more general-purpose processors and/or dedicated processors, and may be configured to perform an analysis on the digital output from the data acquisition unit 155. An output interface may be configured to transmit output from the computing system to a display. The computing system 150 may be further configured to send trigger signals to any of the laser 145, the data acquisition unit 155, and the photodetector 165.

In operation, the sample 170 is placed on the platform 175 for observation of desired endogenous tissues of the sample 170. The surface area of the sample 170 to be imaged may be covered with a transparent liquid material such as a layer of mineral oil, for example. In one example embodiment, the layer of mineral oil may be approximately 2 mm thick. The layer of mineral oil facilitates the detection of the photoacoustic signal, and serves to keep the optical pathlength (OPL) difference between the sample arm 112 and the reference arm 114 in the system 100 to within the coherence length of the light source 110. The layer of mineral oil may act as a reflector.

The light source 110 is directed through the nonreciprocal optical element 115 to the fiber coupler 120 which splits the light into the two arms 112 and 114, the reference arm 114 being directed at the reference mirror 125 and the sample arm 112 or OCT probe beam being directed at the sample 170.

The sample arm 112 and the beam emitted from the laser 145 are combined together by the dichroic mirror 130 and are then focused by the third lens 142 onto the sample 170.

The sample arm 112 is focused onto the layer of mineral oil and the beam from the laser 145 is focused onto the sample 170 beneath the layer of mineral oil. The beam from the laser 145 excites biological tissues of the sample 170, causing the sample 170 to emit photoacoustic signals. The photoacoustic signals are directed through the dichroic mirror 130 to the fiber coupler 120 and the nonreciprocal optical element 115, along with the reflected light from the reference mirror 125, and are then coupled into the photodetector 165. The photodetector 165 rejects common-mode light intensity noises from the received photoacoustic signals, and then feeds the processed photoacoustic signals to the signal processing unit 160 for separation of any low frequency signals from the photoacoustic signals. The signal processing unit 160 feeds the signals to the data acquisition unit 155. The data acquisition unit changes the signals to digital information and then sends the digital information to the computing system 150 for further processing, as will be described with reference to FIGS. 2a-4.

The highest sensitivity to detect a vibration in a sample corresponds to an OPL difference at $k\pi \pm \pi/2$, for example, the zero voltage crossing points for balanced detection. However, ambient vibrations, such as building vibration and room temperature fluctuation, often cause an additional OPL change, leading to a fluctuating sensitivity for the system 100. To mitigate the problem of ambient vibrations, a synchronization method may be used to lock the system 100 working at its highest sensitivity to the layer of oil displacement caused by photoacoustic signals. The highest sensitivity of the system 100 to vibrations is at the point when the OPL equals $k\pi \pm \pi/2$. The computing device 150 may trigger the laser 145 when the output signal of the photodetector 165 is at zero voltage and may at the same time trigger the data acquisition unit 155 to sample the photoacoustic signals. This serves the purpose of locking the system 100 to its highest sensitivity.

The system 100 provides the capacity to reconstruct cross-sectional images on an object from its projections. Two-dimensional data is derived from a three-dimensional body, such as the sample 170, to construct a slice image of the body's internal structure. In OCT, multiple parallel LCI scans may be performed to generate the two-dimensional image. Additionally, an OCT system may perform imaging separate from the photoacoustic imaging, and OCT images may be co-registered with the photoacoustic images. The OCT image is based on light scattering, and may represent the morphological information of the tissue cross-section. The photoacoustic image is based on absorption, and may represent the distribution of endogenous absorbers within the tissue cross-section.

Figure 2A:
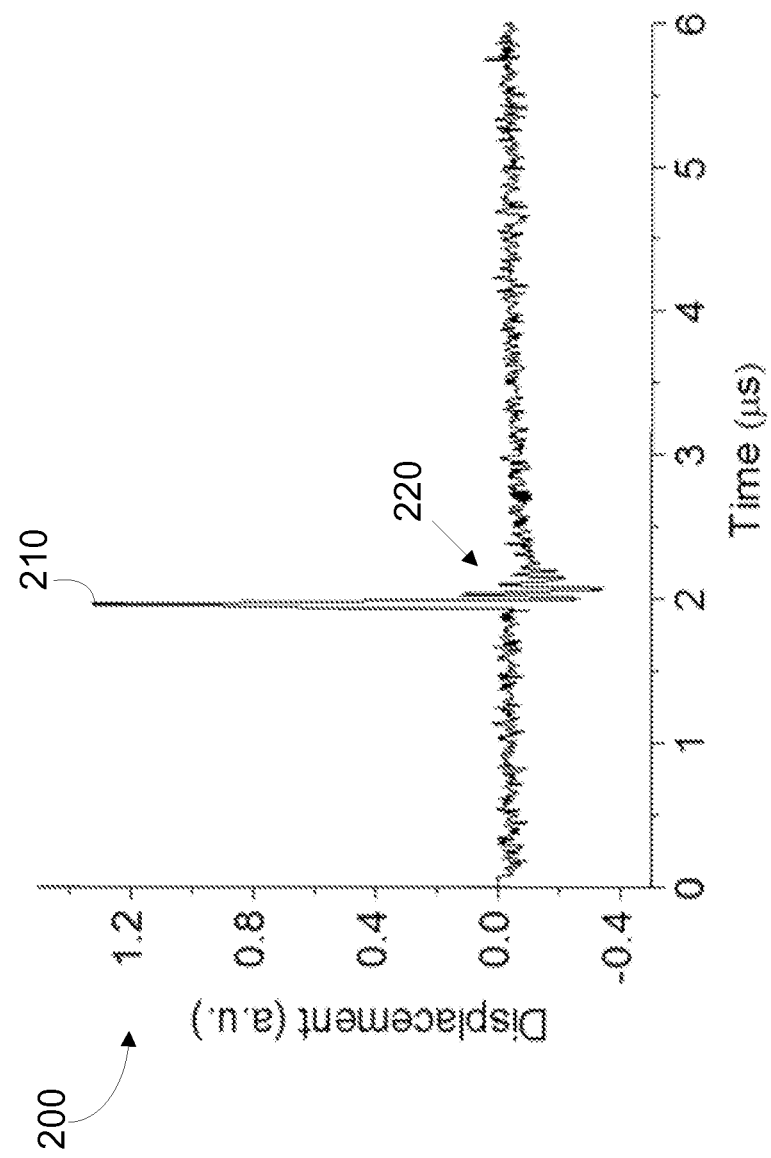
FIG. 2a depicts a graph illustrating the transient displacement of photoacoustic signals from a sample using the photoacoustic imaging system of FIG. 1 over time, in accordance with at least one embodiment.

FIG. 2a depicts a graph 200 illustrating the transient displacement of a photoacoustic signal from a sample using the photoacoustic imaging system of FIG. 1, in accordance with at least one embodiment. The graph 200 may be generated by a computing system such as the computing system 150 in FIG. 1. In the graph 200 of FIG. 2a, the displacement of the photoacoustic signals from a sample of black tape is plotted over time.

At about 2 μs, the main peak 210 of the displacement occurs, and soon thereafter low-amplitude motions 220 occur. The low-amplitude motions 220 result from the multiple reflections of ultrasound waves between the two surfaces of the black tape. The full width at half maximum of the detected photoacoustic signal is about 40 ns, meaning that the axial resolution of the system is 60 μm (calculated with a sound speed of 1.5 mm/μs). The lateral resolution of the system is about 30 μm. Both the axial and lateral resolutions are dependent upon the focus spot size of a probe beam and an excitation laser beam, such as the such as sample arm 112 and the beam emitted from the laser 145 as described with reference to FIG. 1, for example. The pulsed photoacoustic signal shown in FIG. 2a corresponds to a frequency span of 17 MHz, indicating that the bandwidth of the system is better than 17 MHz. For ultrasound detection with optical interferometric methods, the bandwidth is mainly dependent on the focus spot size of the probe beam and is limited by the upper frequency cutoff of the photodetector. The detection bandwidth for the photoacoustic signal may be improved by either a use of higher speed photodetectors or a decrease of the probe beam spot size, or both.

Figure 2B:
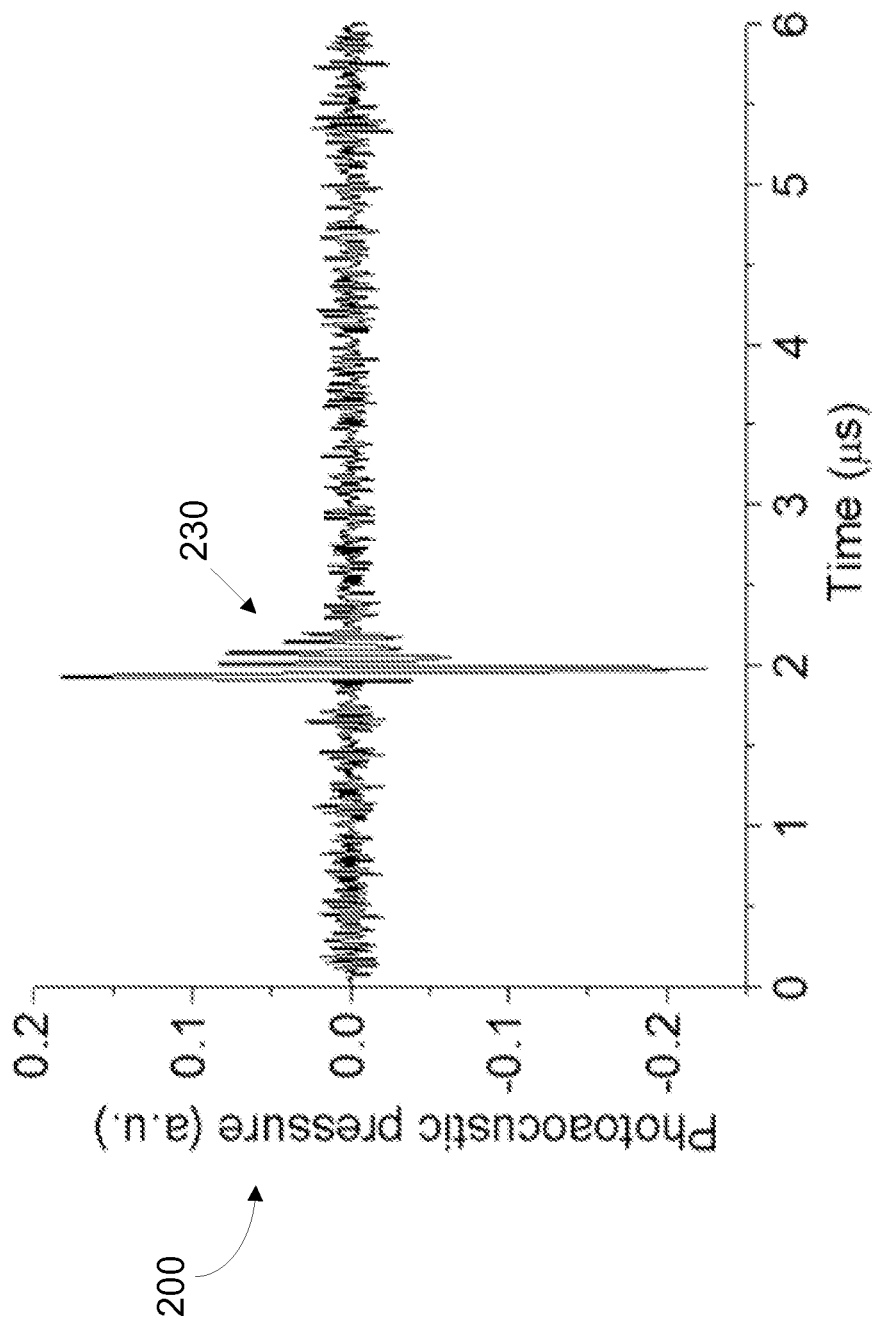
FIG. 2b depicts a graph illustrating the transient pressure corresponding to the transient displacement of FIG. 2a, in accordance with at least one embodiment.

FIG. 2b depicts a graph illustrating the transient pressure corresponding to the transient displacement of FIG. 2a, in accordance with at least one embodiment. The photoacoustic pressure shown in FIG. 2b is the first derivative of the displacement shown in FIG. 2a. The multiple echoes within the sample, labeled 230, correspond to the low-amplitude motions 220 of FIG. 2a.

Images of the sample may be reconstructed by a computing system, such as the computing system 150 of FIG. 1, from the information provided in FIGS. 2a-b.

Figures 3A, 3B:
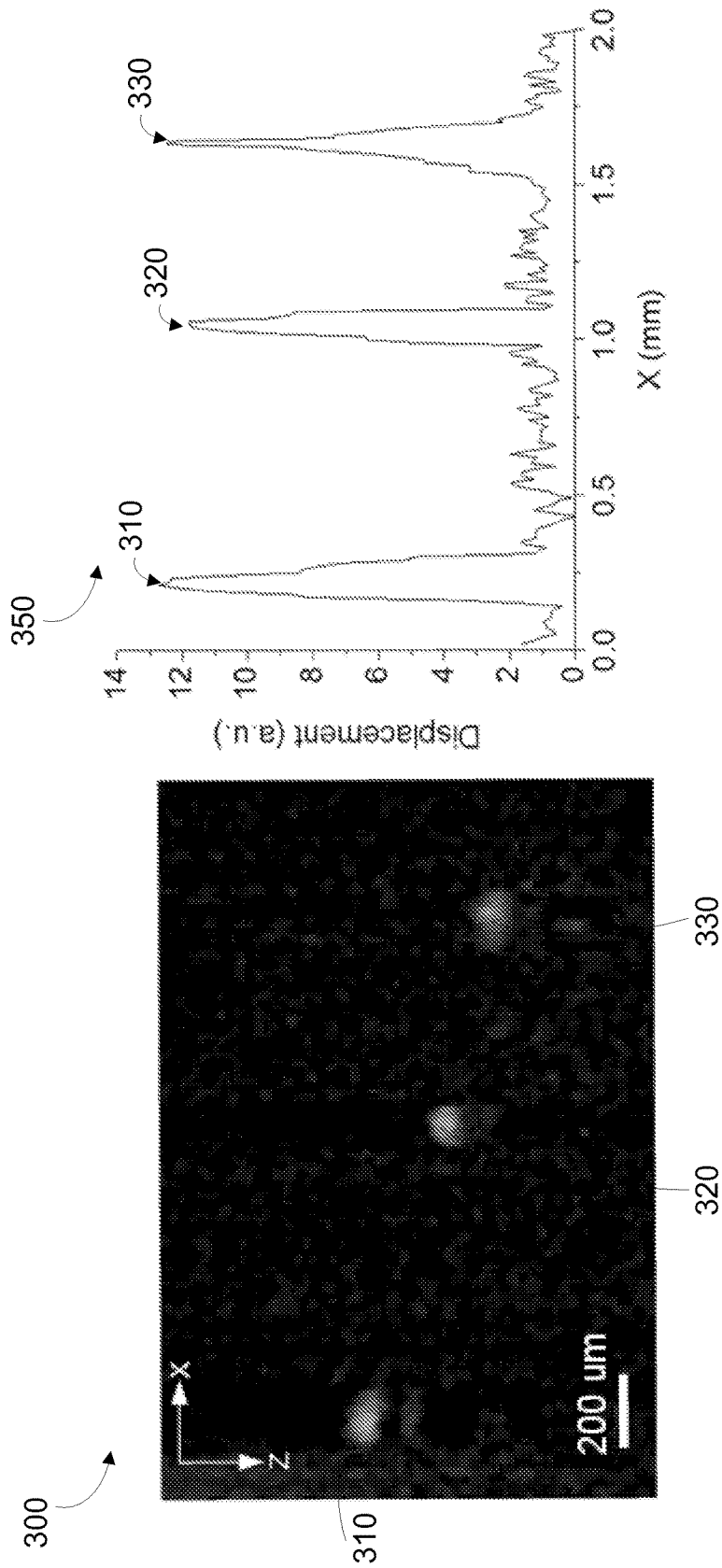
FIG. 3a depicts an example B-scan image generated from the system of FIG. 1, in accordance with at least one embodiment.
FIG. 3b depicts a graph illustrating a maximum intensity projection along the depth of the tissues within the sample of the image generated in FIG. 3a, in accordance with at least one embodiment.

FIG. 3a depicts an example B-scan image 300 generated from a system such as the system 100 of FIG. 1 and information provided as described with reference to FIGS. 2a-b, for example. The image 300 may be projected onto a display associated with the computing system 100 of FIG. 1. The image 300 was taken from a scattering phantom generated from three hairs 310, 320, and 330 embedded within a scattering gel at depths approximately between 0.5 mm and 1.0 mm. The scattering gel in the example of FIG. 3a was made of agar mixed with 1% intralipid to give a scattering background similar to typical highly scattering biological tissue.

The image 300 was taken along the x-axis, nearly perpendicular to the hair axes and spanning a width of 2 mm with 10 μm spacing between adjacent axial scans. The z-axis in the image 300 of FIG. 3a indicates the depth. The full width at half maximum for each of the three hairs 310, 320, and 330 is about 110 μm, 80 μm, and 60 μm, respectively, approximately the same as the sizes measured by a precision caliper. The signal to background noise ratio was evaluated at about 12.

FIG. 3b depicts a graph 350 illustrating a maximum intensity projection along the depth of the tissues within the sample of the image generated in FIG. 3a, in accordance with at least one embodiment. In FIG. 3b, the displacement detected for each hair 310, 320, and 330 is plotted over a period of time.

Figure 4:
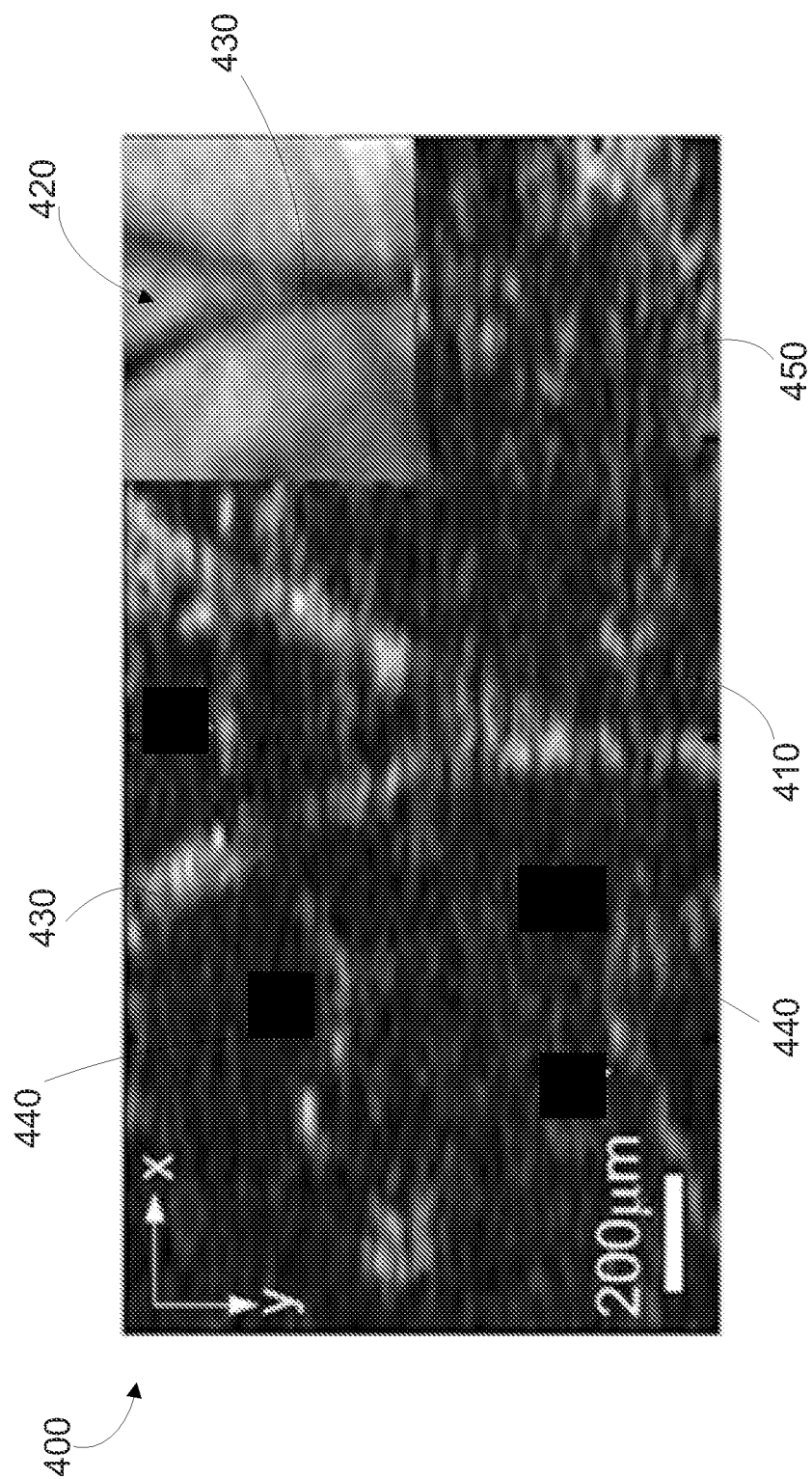
FIG. 4 depicts an example image of blood vessels within a mouse pinna in vitro, generated from the photoacoustic system of FIG. 1, in accordance with at least one embodiment.

FIG. 4 depicts an example image 400 of blood vessels within a mouse pinna in vitro, generated from a photoacoustic system such as the system 100 of FIG. 1, in accordance with at least one embodiment. The image 400 contains an image portion generated via photoacoustic imaging, i.e., a photoacoustic image 410 and a photograph 420 of the pinna for comparison. To generate the image portion generated via photoacoustic imaging 410, a dissected mouse pinna may be placed flat on an imaging platform, such as the platform 175 of FIG. 1. The pinna may be covered with a layer of transparent liquid as described with reference to FIG. 1. The photoacoustic image 410 shows blood vessels within the pinna, and was obtained from an area of approximately 1×2 $mm^2$ on the pinna. The photograph 420 was digitally enhanced to more clearly show the blood vessels on the pinna. As depicted, the photograph 420 corresponds well with the photoacoustic image 410. Y-junction blood vessels 430 are shown in both the photograph 420 and the photoacoustic image 410. The photoacoustic image 410 additionally shows two small vessels 440 that are not visible in the photograph 420. Speckle-like background signals 450 in the photoacoustic image 410 may be due to the pigments that exist within the skin of the pinna.

Figure 5:
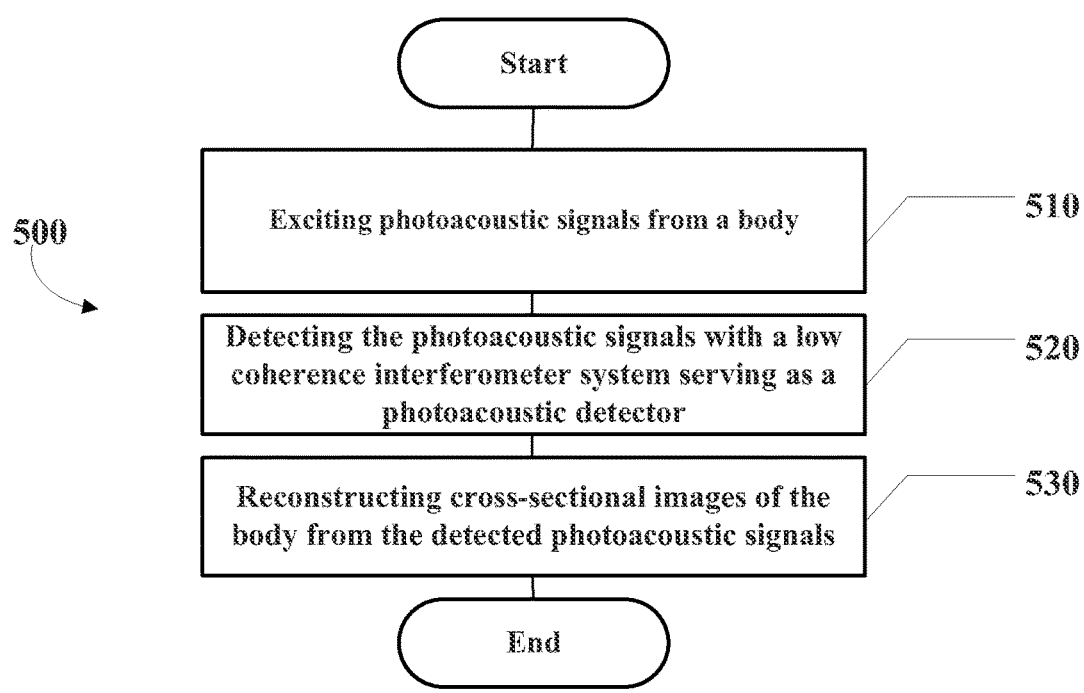
FIG. 5 depicts a simplified flow diagram of an example method that may be carried out to create an image of an endogenous tissue, in accordance with at least one embodiment.

FIG. 5 depicts a simplified flow diagram of an example method that may be carried out to create an image of an endogenous tissue, in accordance with at least one embodiment. Method 500 shown in FIG. 5 presents an embodiment of a method that, for example, could be used with the system 100.

In addition, for the method 500 and other processes and methods disclosed herein, the depicted flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, such as a storage device including a disk or hard drive. The computer readable medium may include a physical and/or non-transitory computer readable medium, for example, such as computer-readable media that stores data for short periods of time like register memory, processor cache, and Random Access Memory (RAM). The physical and/or non-transitory computer readable medium may also include secondary or persistent long term storage, such as read only memory (ROM), optical or magnetic disks, and/or compact-disc read only memory (CD-ROM). The computer readable medium may also be any other volatile or non-volatile storage system. The computer readable medium may be considered a tangible storage device or other article of manufacture, for example. Alternatively, program code, instructions, and/or data structures may be transmitted via a communications network via a propagated signal on a propagation medium (e.g., electromagnetic wave(s), sound wave(s), etc.).

Initially, the method 500 includes exciting photoacoustic signals from a body, at block 510. A laser, such as the laser 145 described with reference to FIG. 1, may be directed onto the body to excite the photoacoustic signals.

The method 500 then includes detecting the photoacoustic signals with an LCI system serving as a photoacoustic detector, at block 520. The LCI system may be an OCT system, and may be the same as or similar to the system 100 of FIG. 1.

The method 500 includes reconstructing cross-sectional images of the body from the detected photoacoustic signals, at block 530. As described with reference to FIG. 1, the detected photoacoustic signals may be processed to remove noise and may be formatted to be used by a computer-readable medium. The formatted signals may then be fed to a computing system, such as the computing system 150, for further processing. The computing system 150 may plot the transient displacement of the body and the corresponding transient pressure over time, as described with reference to FIGS. 2a-b, and may use the information to reconstruct a cross-sectional image of the body. The reconstructed image may resemble the photoacoustic image 410 described with reference to FIG. 4.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

What is claimed is:

1. A method for photoacoustic imaging comprising:
    exciting, through delivery of a laser onto a body, photoacoustic signals from the body;
    detecting the excited photoacoustic signals that have propagated to the surface of the body with a low coherence interferometer system serving as a noncontact photoacoustic detector, wherein the photoacoustic signals are directed into a photodetector of the low coherence interferometer system; and
    reconstructing cross-sectional images of the body from the detected photoacoustic signals.

2. The method of claim 1, wherein the detecting the photoacoustic signals with a low coherence interferometer system comprises detecting with an optical coherence tomography system.

3. The method of claim 2, wherein the optical coherence tomography system comprises a probe beam, and the detecting comprises:
    focusing the probe beam onto the surface of the body; and
    detecting transient motion of the surface of the body resulting from the photoacoustic signals excited from the body.

4. The method of claim 3, wherein the detecting further comprises:
    treating the body with a layer of substantially transparent liquid material to facilitate detection of the photoacoustic signals.

5. The method of claim 3, wherein detecting the photoacoustic signals further comprises:
    increasing a detection bandwidth for each of the photoacoustic signals by decreasing the size of the probe beam of the optical coherence tomography system.

6. The method of claim 3, wherein the optical coherence tomography system further comprises a dichroic mirror that directs the probe beam and the laser beam at the body.

7. The method of claim 2, further comprising:
    generating images of the body using optical coherence tomography; and
    co-registering images of the body using optical coherence tomography with the cross-sectional images of the body from the detected photoacoustic signals.

8. The method of claim 2, wherein the optical coherence tomography system is a time domain optical coherence tomography system operating in a homodyne mode, and wherein the time domain optical coherence tomography system comprises a light source in communication with a nonreciprocal optical element and a fiber coupler.

9. The method of claim 8, wherein the photodetector is a balanced photodetector and wherein detecting the photoacoustic signals further comprises:
    coupling output electric signals from the nonreciprocal optical element and the fiber coupler into the balanced photodetector to reject noise from the photoacoustic signals.

10. The method of claim 9, further comprising:
    sending a trigger signal to a data acquisition unit for sampling the photoacoustic signals and to an excitation laser for delivering a laser beam to the body when a DC output signal from the balanced photodetector crosses a threshold.

11. The method of claim 2, wherein detecting the photoacoustic signals further comprises:
increasing a detection bandwidth for each of the photoacoustic signals by increasing the speed of the photodetector of the optical coherence tomography system.

12. The method of claim 1, wherein detecting the photoacoustic signals further comprises:
sending the photoacoustic signals to a data acquisition unit.

13. The method of claim 1, wherein detecting the photoacoustic signals further comprises:
separating the photoacoustic signals from residual ambient vibrations via a high-pass filter.

14. The method of claim 1 further comprising:
deriving a corresponding photoacoustic pressure from a detected photoacoustic signal of the detected photoacoustic signals.

15. A system for noncontact photoacoustic imaging comprising:
an optical coherence tomography probe;
a laser configured to excite photoacoustic signals from a sample;
a nonreciprocal optical element;
a photodetector; and
a coupler configured to couple and send the photoacoustic signals that have propagated to the surface of the sample and reflected light to the photodetector;
wherein the photodetector is connected with a data acquisition unit and a computing system for image reconstruction of the sample from the photoacoustic signals.

16. The system of claim 15, wherein the system comprises a time domain optical coherence tomography system operating in a homodyne mode.

17. A physical computer-readable storage medium having stored thereon instructions executable by a device to cause the device to perform functions comprising:
exciting, through delivery of an excitation laser onto a body, photoacoustic signals from the body;
detecting the photoacoustic signals that have propagated to the surface of the body with an optical coherence tomography system, wherein the optical coherence tomography system serves as a noncontact photoacoustic detector;
reconstructing cross-sectional images of the body from the detected photoacoustic signals.

18. The physical computer readable storage medium of claim 17, wherein the functions further comprise:
combining a probe beam and the excitation laser with a dichroic mirror;
focusing the probe beam onto the surface of the body;
focusing the excitation laser into the body; and
detecting transient motion of the surface of the body resulting from the photoacoustic signals emitted from within the body.

19. The physical computer readable storage medium of claim 18 wherein the functions further comprise:
focusing the probe beam and the excitation laser by a first lens and a second lens.

20. The physical computer readable storage medium of claim 17, wherein the optical coherence tomography system is a time domain optical coherence tomography system operating in a homodyne mode and comprising a light source, an optical circulator, and a fiber coupler.

* * * * *